US009844483B2

(12) United States Patent
Barlow et al.

(10) Patent No.: US 9,844,483 B2
(45) Date of Patent: Dec. 19, 2017

(54) MEDICAL DEVICE FOR THERAPEUTIC STIMULATION OF THE VESTIBULAR SYSTEM

(75) Inventors: Steven M. Barlow, Lawrence, KS (US); Douglas S. Kieweg, Lawrence, KS (US); Emily Zimmerman, Demver, CO (US)

(73) Assignee: The University of Kansas, Lawrence, KS (US)

( * ) Notice: Subject to any disclaimer, the term of this patent is extended or adjusted under 35 U.S.C. 154(b) by 953 days.

(21) Appl. No.: 14/112,509

(22) PCT Filed: Apr. 19, 2012

(86) PCT No.: PCT/US2012/034238
§ 371 (c)(1),
(2), (4) Date: Oct. 17, 2013

(87) PCT Pub. No.: WO2012/145502
PCT Pub. Date: Oct. 26, 2012

(65) Prior Publication Data
US 2014/0046231 A1    Feb. 13, 2014

Related U.S. Application Data

(60) Provisional application No. 61/476,943, filed on Apr. 19, 2011.

(51) Int. Cl.
*A61M 11/00* (2006.01)
*A61H 1/00* (2006.01)
(Continued)

(52) U.S. Cl.
CPC ............. *A61H 1/001* (2013.01); *A61B 5/024* (2013.01); *A61B 5/0816* (2013.01);
(Continued)

(58) Field of Classification Search
CPC .......... A61H 1/00; A61H 1/001; A61H 1/003; A61H 1/005; A61H 23/00; A61H 1/02;
(Continued)

(56) References Cited

U.S. PATENT DOCUMENTS 1,693,633 A * 12/1928 Allen .................... B60N 2/2848
280/31
2,675,285 A * 4/1954 Eselle .................. A61G 13/009
108/147.22
(Continued)

FOREIGN PATENT DOCUMENTS

EP        2092882 A3    4/2012
WO     95/023722       9/1995
(Continued)

OTHER PUBLICATIONS

John N. I. Dieter and Eugene K. Emory, Supplemental Stimulation of Premature Infants: A Treatment Model, vol. 22, No. 3, 1997, pp. 281-295, Journal of Pediatric Psychology, Emory University.
(Continued)

*Primary Examiner* — Steven Douglas
(74) *Attorney, Agent, or Firm* — Maschoff Brennan

(57) ABSTRACT

A method for providing vestibular stimulation includes: providing an infant in a vestibular stimulation device; associating sensors to the infant; moving the vestibular stimulation device to provide vestibular stimulation treatment; and obtaining sensor data during the treatment. The vestibular stimulation device includes a holder member; a platform; a mechanical system coupling the holder member to the platform; sensors configured to detect one or more parameters of the infant; and a computing system having a user input and/or output interface operably coupled to the mechanical system and the sensors to provide mechanical data to the mechanical system in order to control movement of the holder member relative to the platform and to collect
(Continued)

the one or more parameters of the living subject from the sensors.

20 Claims, 12 Drawing Sheets

(51) Int. Cl.
| | |
|---|---|
| A61B 5/024 | (2006.01) |
| A61B 5/08 | (2006.01) |
| A61B 5/1455 | (2006.01) |
| A61B 5/113 | (2006.01) |
| A61M 21/00 | (2006.01) |
| A61G 5/10 | (2006.01) |
| A61J 17/00 | (2006.01) |

(52) U.S. Cl.
CPC .......... *A61B 5/1135* (2013.01); *A61B 5/1455* (2013.01); *A61H 1/005* (2013.01); *A61M 21/00* (2013.01); *A61G 5/101* (2013.01); *A61H 2201/0142* (2013.01); *A61H 2201/0149* (2013.01); *A61H 2201/0173* (2013.01); *A61H 2201/1666* (2013.01); *A61H 2201/501* (2013.01); *A61H 2201/5038* (2013.01); *A61H 2201/5064* (2013.01); *A61H 2201/5084* (2013.01); *A61H 2201/5097* (2013.01); *A61H 2230/065* (2013.01); *A61H 2230/208* (2013.01); *A61H 2230/425* (2013.01); *A61H 2230/625* (2013.01); *A61J 17/001* (2015.05); *A61M 2021/0022* (2013.01); *A61M 2230/205* (2013.01); *A61M 2230/42* (2013.01); *A61M 2230/62* (2013.01); *A61M 2230/63* (2013.01); *A61M 2240/00* (2013.01)

(58) Field of Classification Search
CPC ........ A61H 2201/00; A61H 2201/0119; A61H 2201/0138; A61H 2201/0149; A61H 2201/12; A61H 2201/1207; A61H 2201/16; A61H 2201/1657; A61H 2201/1664; A61H 2201/1666; A61H 2201/5058; A61H 2201/5079; A61H 2201/5084; A61H 2203/00; A61H 2203/04; A61H 2203/0425; A61H 2203/0431; A61H 2230/00; A61H 2230/40; A61H 2230/405
See application file for complete search history.

(56) References Cited

U.S. PATENT DOCUMENTS

| | | | | |
|---|---|---|---|---|
| 3,284,126 A * | 11/1966 | Piazza | .................. | A47C 17/163 280/657 |
| 3,658,052 A * | 4/1972 | Alter | ...................... | A61B 5/113 340/551 |
| 3,676,881 A * | 7/1972 | Duprey | .................. | A61G 7/005 5/510 |
| 3,944,241 A * | 3/1976 | Epelbaum | ................ | B62B 7/12 280/30 |
| 4,619,270 A * | 10/1986 | Margolis | ................ | A61H 1/001 600/534 |
| 4,762,331 A * | 8/1988 | Tucker | ...................... | B62B 7/12 280/30 |
| 4,934,997 A | 6/1990 | Skakas | | |
| 4,947,832 A | 8/1990 | Blitzer | | |
| 5,480,170 A * | 1/1996 | Kaiser, II | ................ | A47B 31/02 108/80 |
| 5,720,079 A * | 2/1998 | Yang | .................... | A47D 13/043 16/35 R |
| 5,853,005 A | 12/1998 | Scanlon | | |
| 6,175,981 B1 * | 1/2001 | Lizama | .................... | A47D 9/02 5/655 |
| 6,446,821 B1 * | 9/2002 | Salisbury | .................. | A61J 9/00 215/11.1 |
| 6,470,200 B2 * | 10/2002 | Walker | ............... | A61B 5/14552 600/323 |
| 6,728,980 B1 * | 5/2004 | Chen | ........................ | A47D 9/02 5/105 |
| 6,789,280 B1 * | 9/2004 | Paul | ........................ | A61G 7/012 5/425 |
| 6,920,656 B2 * | 7/2005 | Roussy | .................. | A61G 7/012 16/19 |
| 6,961,968 B2 * | 11/2005 | Clapper | .................... | A47D 5/00 5/655 |
| 7,333,020 B2 * | 2/2008 | Cohen | .................... | A61B 5/038 340/573.1 |
| 8,240,699 B2 * | 8/2012 | Zhong | ..................... | A47D 9/00 16/34 |
| 8,340,757 B2 | 12/2012 | Chan et al. | | |
| 8,621,691 B1 * | 1/2014 | Alsaffar | ........................... | 5/613 |
| 9,149,681 B2 * | 10/2015 | Smead | .................. | A63B 21/02 |
| 9,192,247 B1 * | 11/2015 | Lu | ........................ | A47D 13/043 |
| 2002/0089140 A1 * | 7/2002 | Lu | ........................ | A47D 13/043 280/87.051 |
| 2005/0085687 A1 | 4/2005 | Mackin et al. | | |
| 2005/0098969 A1 * | 5/2005 | Waldman | .................. | A47D 9/00 280/47.38 |
| 2006/0085919 A1 * | 4/2006 | Kramer | .................. | A47C 7/022 5/713 |
| 2007/0100263 A1 | 5/2007 | Merfeld | | |
| 2007/0167985 A1 | 7/2007 | Kirby | | |
| 2008/0269629 A1 * | 10/2008 | Reiner | .................. | A61B 5/4836 600/544 |
| 2009/0217458 A1 * | 9/2009 | Lord | ...................... | A47D 13/08 5/655 |
| 2011/0028872 A1 * | 2/2011 | Kevin | .................... | G09B 19/00 601/86 |
| 2011/0045079 A1 | 2/2011 | Edwards | | |
| 2014/0296661 A1 * | 10/2014 | Zwartkruis-Pelgrim | | A61B 5/228 600/301 |

FOREIGN PATENT DOCUMENTS

| | | |
|---|---|---|
| WO | 98/039996 | 9/1998 |
| WO | 20070113871 | 10/2007 |

OTHER PUBLICATIONS

A. F. Korner, P. Schneider and T. Forrest, Effects of Vestibular-Proprioceptive Stimulation on the Neurobehavioral Development of Preterm Infants: A Pilot Study, 1983, vol. 14, pp. 170-175, Hippokrates Verlag Gmb K.

T. Farrimond, Sudden Infant Death Syndrome and Possible Relation to Vestibular Function, Perceptual and Motor Skills, 1990, 71, 419-423, 5 pages, University of Waikato.

Anneliese F. Korner, Ph.D., Helena C. Kraemer, Ph.D., M. Ellen Haffner, B.A., and Lorna M. Cosper, R.N., Effects of Waterbed Flotation on Premature Infants: A Pilot Study, 8 pages, From the Department of Psychiatry, Stanford University School of Medicine, Stanford, California.

E. Zimmerman and SM Barlow, The Effects of Vestibular Stimulation Rate and Magnitude of Acceleration on Central Pattern Generation for Chest Wall Kinematics in Preterm Infants, 7 pages, Journal of Perinatology (2012) 32, 614-620, 2012 Nature America, Inc., www.nature.com/jp.

* cited by examiner

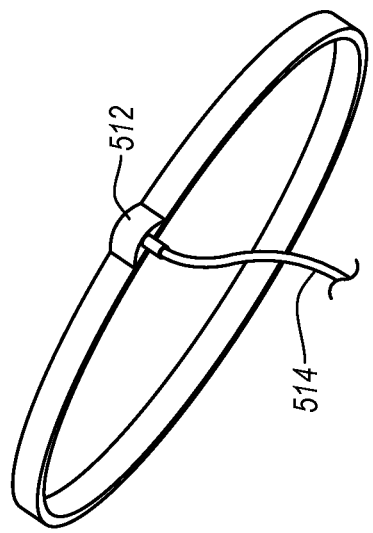
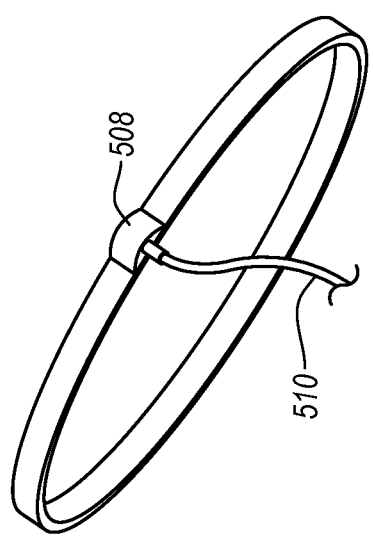
Fig. 5B

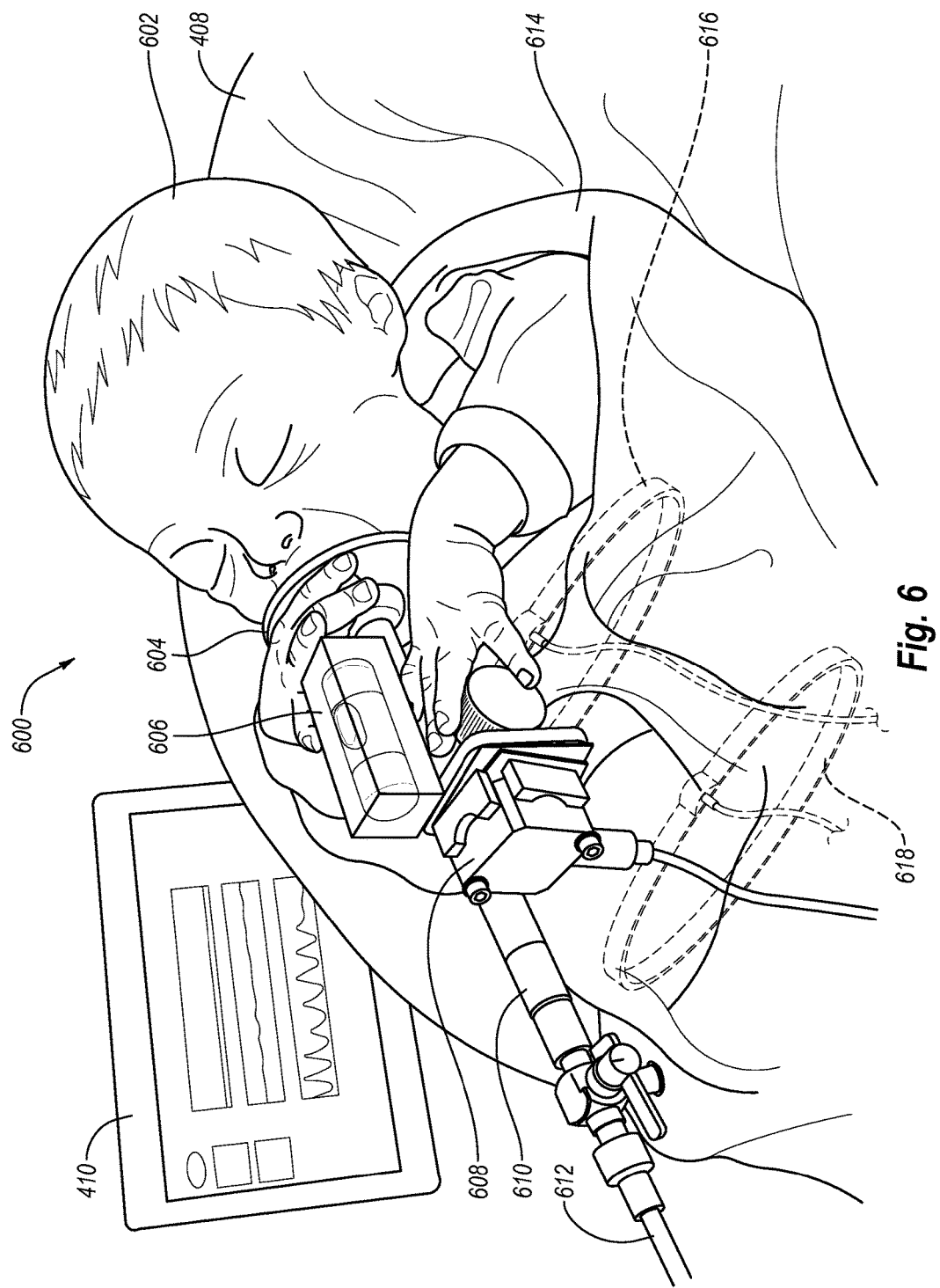

MEDICAL DEVICE FOR THERAPEUTIC STIMULATION OF THE VESTIBULAR SYSTEM

CROSS-REFERENCE

This patent application claims benefit of U.S. Provisional Application Ser. No. 61/476,943, filed on Apr. 19, 2011, which provisional application is incorporated herein by specific reference in its entirety.

GOVERNMENT RIGHTS

This invention was made with government support under 3R01 DC003311-6A1S1 and P30 DC005803 awarded by the National Institutes of Health. The government has certain rights in the invention.

BACKGROUND

Respiratory complications are one of the most common and immediate problems facing premature infants. These complications range from a mild oxygen need to an immense oxygen dependency that can result in the scarring of lung tissue. Respiratory complications not only prolong the time spent in the neonatal intensive care unit (NICU), but can also hinder lung and brain development. Therapies designed to reduce respiratory needs and increase the ability for premature infants to breathe independently are vital for this fragile population. The isolettes and cribs in the NICU severely limit the newborn's continued experience with imposed motion, acceleration, and changing orientation to gravitational loads. In utero, the mother typically provides the fetus with a near continuous stream of vestibular stimulation daily through routine motor activities such as walking, driving a car, sitting, sleeping, rolling over, postural changes, breathing, etc. These forms of vestibular stimulation are hypothesized to influence the brain stem reticular formation with indirect neural pathways that may influence postural motor control, state control, and respiratory patterning.

Thus, it would be beneficial to develop a device that can systematically introduce physiologically salient vestibular stimulation to a newborn that is otherwise faced with the prospect of laying stationary for extended periods of time in a crib or isolette.

SUMMARY

In one embodiment, a vestibular stimulation device can include: a holder member adapted to hold a living subject; a platform; a mechanical system operably coupling the holder member to the platform such that the mechanical system is capable of moving the holder member in one or more directions relative to the platform; one or more sensors configured to be associated with the living subject and detect one or more parameters of the living subject; and a computing system having a user input and/or output interface operably coupled to the mechanical system and the one or more sensors so as to provide mechanical data to the mechanical system in order to control movement of the holder member relative to the platform and to collect the one or more parameters of the living subject from the one or more sensors. The holder member can be configured as a crib, cradle, isolette, bed, chair, table top with one or more restraints, or combination thereof. The living subject can be an infant.

In one embodiment, the mechanical system can be configured to move the compartment in the directions of an X-axis, Y-axis, and/or Z-axis. Also, the mechanical system is configured for one or more of the following: to move the holder member in a sinusoidal displacement at a rate of from about 0.5 to about 0.95 Hz; to move the holder member with accelerations from about 0.21 to about 0.51 $m/s^2$; to move the holder member with sinusoidal cycles from about 30 to about 60 cycles per minute (cpm); to move the holder member with a displacement from 20 mm to about 90 mm; to move the holder member so as to simulate motion, acceleration, and changing orientation to gravitational loads; to move the holder member at frequencies with a range of chest wall motion for an infant human living subject; or to move the holder member at frequencies equivalent to about 40 to 60 breaths per minute (BPM).

In one embodiment, the mechanical system can include a linear motor and a glider track configured to move the holder member linearly with respect to the platform in one or more sinusoidal movement patterns under control of the computing system. Also, the one or more sensors can be selected from a sensor configured to detect acceleration, a sensor configured to detect breaths per minute (BPM), a sensor configured to detect suck displacement, a sensor configured to detect oromotor control, a sensor to measure pulse, oxygenation of hemoglobin, blood oxygen saturation, living subject head tilt, or combinations thereof. The computing system can be configured to receive, store, and process data of the one or more sensors independently or in combination.

In one embodiment, one or more wheels operably coupled the platform and one or more lift-locks coupled to the platform such that the platform has a mobile configuration when the lift-locks are disengaged and a stationary configuration when the lift-locks are engaged so as to elevate the wheels above ground.

In one embodiment, a kit can include the vestibular stimulation device and a pacifier having an accelerometer sensor configured to detect acceleration. Also, the kit can include a pillow configured to incline the infant when located on the holder member.

In one embodiment, a pacifier accelerometer can include: a pacifier having a nipple; an accelerometer operably coupled to the pacifier opposite of the nipple, the accelerometer having a longitudinal axis configured to be in a horizontal plane; and a level operably coupled to the pacifier and/or accelerometer in a position so as to be parallel to the longitudinal axis such that the level is horizontal when the longitudinal axis of the accelerometer is horizontal. In one aspect, the accelerometer is mounted opposite of the pacifier portion with the level mounted on the accelerometer.

In one embodiment, a method for providing vestibular stimulation to a living subject can include: providing a vestibular stimulation device; placing a living subject on the holder member; associating one or more sensors to the living subject; moving the holder member in the one or more directions so as to provide vestibular stimulation treatment to the living subject; and obtaining sensor data from the one or more sensors.

In one embodiment, the vestibular stimulation is provided to an infant as the living subject in an amount and number of times sufficient for: treating a respiratory complication in an infant; improving formation of indirect neural pathways in the infant; improving postural motor control in the infant; improving state control in the infant; improving respiratory patterns in the infant; or improving oromotor development in the infant.

In one embodiment, the method performed on an infant can include selecting the infant to have one or more of the following characterizations: the infant is dependent on significant amounts of oxygen; the infant has a respiratory complication; the infant is in need of improved formation of indirect neural pathways; the infant is in need of improved postural motor control; the infant is in need of improved state control; the infant is in need of improved respiratory patterns; or the infant is in need of improved oromotor development.

In one embodiment, the method can include one or more of the following: moving the holder member in the X-axis, Y-axis, and/or Z-axis; moving the holder member in a sinusoidal displacement at a rate of from about 0.5 to about 0.95 Hz; moving the holder member with accelerations from about 0.21 to about 0.51 $m/s^2$; moving the holder member with sinusoidal cycles from about 30 to about 60 cycles per minute (cpm); moving the holder member with a displacement from 20 mm to about 90 mm; moving the holder member so as to simulate motion, acceleration, and changing orientation to gravitational loads; moving the holder member at frequencies with a range of chest wall motion for an infant human living subject; or moving the holder member at frequencies equivalent to about 40 to 60 breaths per minute (BPM).

In one embodiment, the method can include collecting, storing, and/or analyzing sensor data. The one or more sensors can be selected from a sensor configured to detect acceleration, a sensor configured to detect breaths per minute (BPM), a sensor configured to detect suck displacement, a sensor configured to detect oromotor control, a sensor to measure pulse, oxygenation of hemoglobin, blood oxygen saturation, living subject head tilt, or combinations thereof.

In one embodiment, the method can include proving the vestibular stimulation treatment before a feeding the infant.

In one embodiment, the method can include one or more of the following: fitting the infant with a respiratory trace device to record chest wall motion, including two soft cloth inductance bands around the rib cage and abdomen, and measuring breaths per minute (BPM); fitting infant with pulse rate and SpO2 signal measuring devices and measuring pulse rate and SpO2 fitting infant with a neonate oxygen sensor and measuring oxygen saturation; or determining a baseline without vestibular stimulation.

FIGURES

FIG. 5B shows an embodiment of respiration sensors;

FIG. 6 shows an embodiment of using a pacifier accelerometer and respiration sensors with a stimulation device;

DETAILED DESCRIPTION

Figure 1:
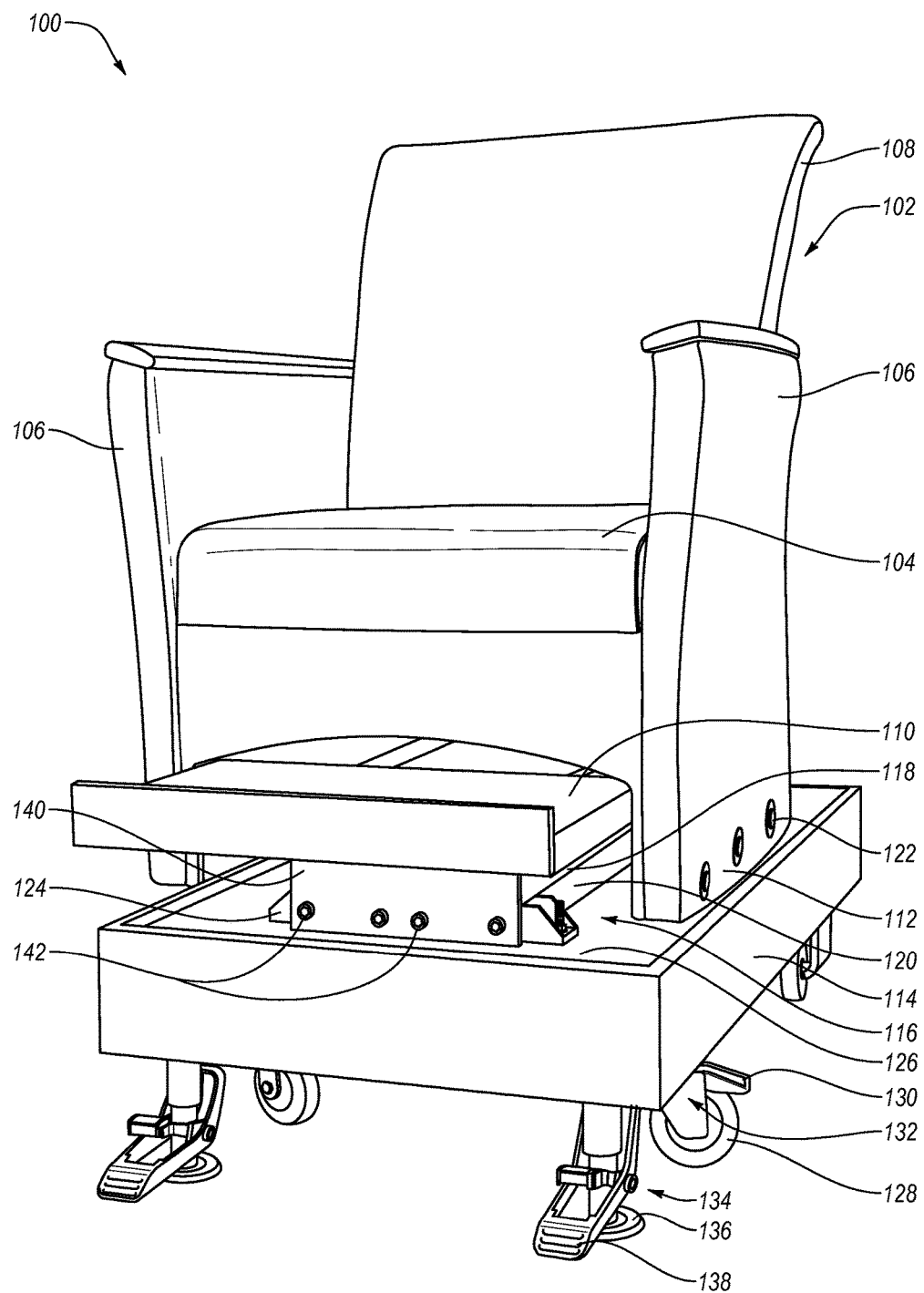
FIG. 1 shows an embodiment of a stimulation device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, it would be beneficial for a device to be configured to be capable of systematically introducing physiologically salient vestibular stimulation to a newborn or other infant child, such as a newborn that is otherwise faced with the prospect of laying stationary for extended periods of time in a crib or isolette. The child can be a pre-term baby or a full-term baby or other human that needs or desires vestibular stimulation. The device can provide vestibular stimulation to the child, and therefore a device capable of creating the vestibular stimulation can be considered a vestibular stimulation device. The vestibular stimulation device can be used in any setting for a child, such as in the NICU for a pre-term infant child, in order to provide or promote a more positive and beneficial vestibular stimulation experience. The vestibular stimulation device can be configured to be compatible with any environment, such as in a hospital in a NICU environment, and can be used to provide vestibular simulation experiences to the child to promote growth and development, such as lung development.

The vestibular stimulation device can be used to overcome or provide a therapy for respiratory complications, among other things, that are common in premature infants. The vestibular stimulation device can provide a suitable therapy for infants that need mild oxygen and also to infants that have an immense oxygen dependency, which can result in the scarring of lung tissue. While the vestibular stimulation device can provide a therapy for respiratory complications and reduce time spent in the NICU, it can also provide a therapy to promote lung and brain development, which is usually inhibited with loss of vestibular stimulus. The vestibular stimulation device can reduce respiratory needs and increase the ability for premature infants to breathe independently. Other uses for the vestibular stimulation devices are described in more detail below.

Typical isolettes and cribs in the NICU severely limit the newborn infant's experience in life by preventing the infant from experiencing imposed motion, acceleration, and changing orientation to gravitational loads. However, the vestibular stimulation device can provide the infant with imposed motion, acceleration, and changing orientation to gravitational loads. When in cribs or isolettes, the infant does not obtain important vestibular stimulation through routine motor activities that can be provided by the mother when in utero, such as walking, driving a car, sitting, sleeping, rolling over, postural changes, breathing, or the like. Also, by staying stationary in a crib or isolate in a NICU, an infant does not experience common vestibular stimulation by typical interaction with other humans in their environment because it is common practice to leave infants in a NICU for extended periods of time (e.g., hours) without significant interaction. The vestibular stimulation device can simulate any normal activities or real life experiences of movement or motion for providing vestibular stimulation to the infant.

When the infant is premature, the vestibular device can restore vestibular stimulation that can positively impact a dormant infant. The vestibular stimulation provided by the vestibular stimulation device may influence the brain stem reticular formation with indirect neural pathways that may influence postural motor control, state control, and respiratory patterning.

The vestibular stimulation device can provide vestibular inputs to an infant that would otherwise be confined to a crib or isolette. Also, the vestibular stimulation device can provide therapy that can improve respiratory and oromotor systems during a critical period for suck and early feeding development in preterm infants. Additionally, the vestibular stimulation device can provide linear acceleration of the vestibular otoliths.

The vestibular stimulation device can be configured in various manners in order to obtain these functionalities and other described herein. Often, the vestibular stimulation device can include a mechanical system that can cause the movement in any degree of freedom. For example, the vestibular stimulation devices can include one or more integrated position-servo motors and digital controllers to generate physiologically appropriate sinusoidal displacements. For example, one integrated position-servo motor can provide linear movement in one direction. As such, three integrated position-servo motors can be used for 3 dimensions. Also, a plurality of integrated position-servo motors can move the vestibular device in a plurality of directions. Other mechanical components can be included in order generate motion in any direction and in any manner to provide vestibular stimulation to the subject.

In the illustrated example provided herein, the vestibular stimulation device is configured as a glider chair that is mounted to a bearing track and an integrated position-servo motor. The servo motor can glide the glider chair in the horizontal plane at salient rates and accelerations. However, the vestibular stimulation device can include any other structure that can hold, contain, retain, or support a subject that needs or receives vestibular stimulation.

FIG. 1 shows an embodiment of a vestibular stimulation device 100. The vestibular stimulation device can include a chair 102 having a chair seat 104, chair arm 106, chair back 108, a foot rest 110, and a chair base 112. The chair 102 can be movably coupled to a platform 114 where a mechanical system 116 is used to moveably couple the chair to the platform 114. The mechanical system 116 can include a chair rail 118 coupled to the chair rail through a chair rail coupler 122. Also, the mechanical system 116 can include a platform 114 can include a platform rail 120 coupled to the platform through a platform rail coupler 124. The mechanical system 116 can include a motor 140 and a motor connector 142 that connects the motor to the chair rail 118 and/or platform rail 120 so as to be capable of moving the chair 102 relative to the platform 114. The platform 114 can include a platform substrate 126 that holds the chair 102 and mechanical system 116. The platform 114 can also include wheels 128 that have a wheel lock 130 and be coupled to the platform 114 via a wheel coupler 132. The platform 114 can also include platform lift-locks 134 that has a lift actuator 138.

Generally, FIG. 1 illustrates a vestibular device in the form of a chair. The chair is attached to a 3-stage linear motor and dual-rail translation stage. Lift-locks permit the user to easily elevate the entire system during use to provide a stable platform that does not move until the lift-locks are released. Medical-grade antibacterial 4" casters permit easy relocation of the vestibular device to individual isolettes within a NICU.

Figure 2A:
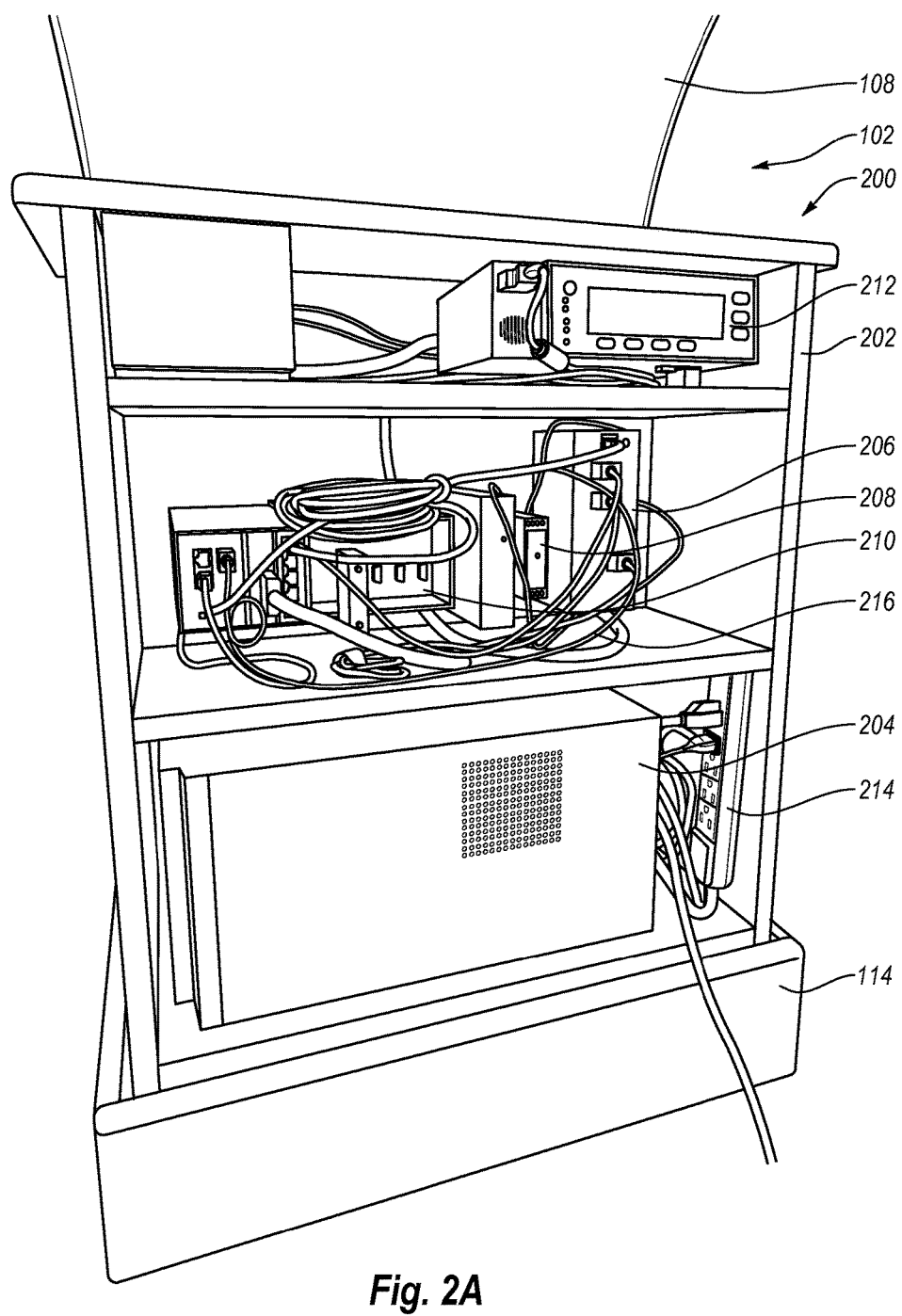
FIG. 2A shows an embodiment of computing devices of a stimulation system.
Figure 2B:
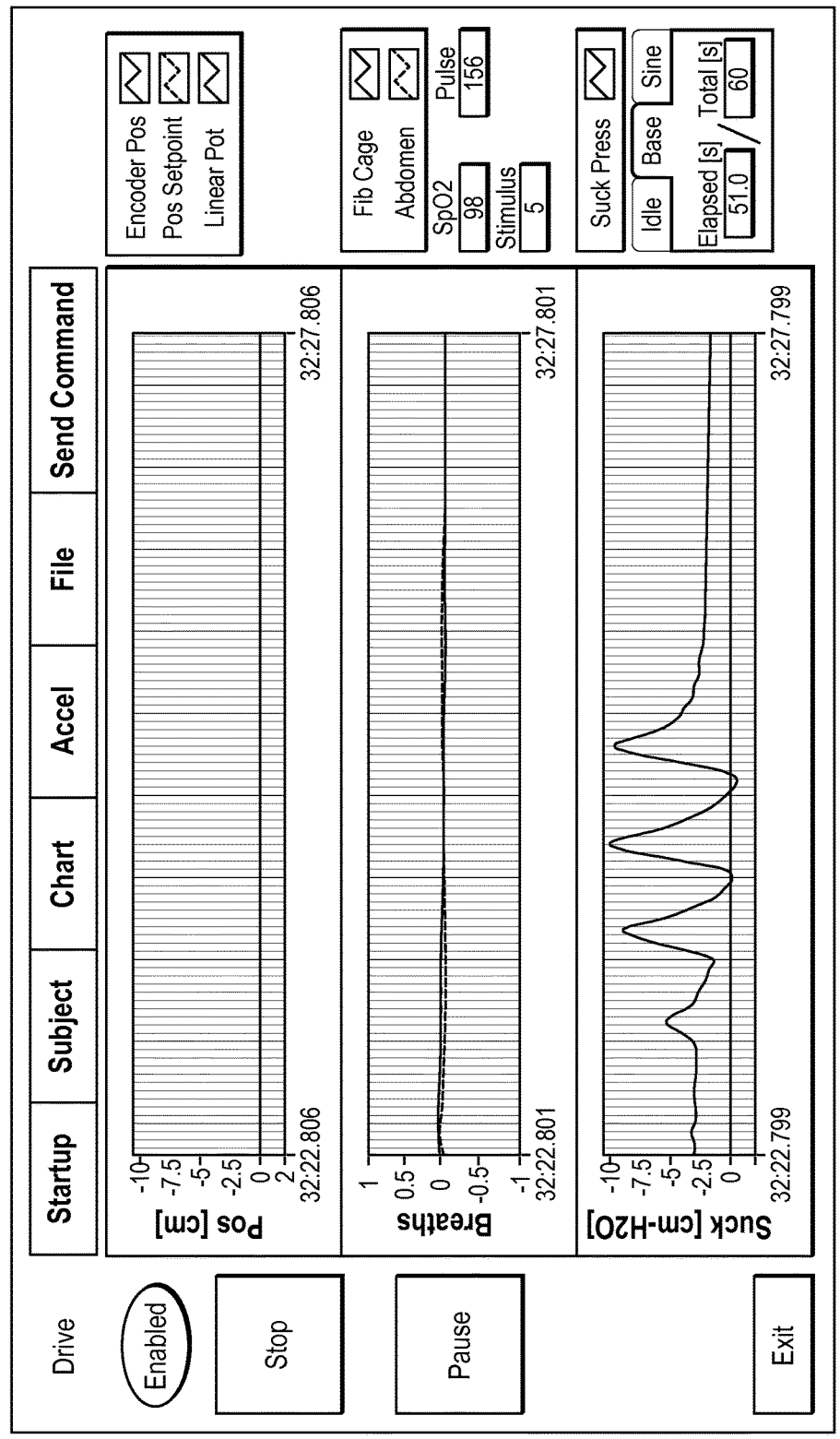
FIG. 2B shows a graphical user interface generated by operating a stimulation system.

FIG. 2A shows an embodiment of computing devices of a computing station 200 of a vestibular stimulation system 100. The computing station 200 can include shelving 202 that can hold an isolation transformer 204, a computing device 206, sensor device 208, motor controller 210, second sensor device 212, a power source 214, and various data connections 216. FIG. 2B shows a graphical user interface generated by operating a vestibular stimulation system 100 that has the computing devices of the computing station 200. The top trace is the glider chair position in cm (e.g., straight line because it is in a baseline condition), second trace down is the Respitrace™ band output (e.g., abdominal output in red and rib cage output in white), and the bottom trace is the suck displacement in cmH20. The SpO2 and Pulse output from the neonatal oxygen sensor are seen in the far right column.

For example, FIG. 2A illustrates a rear view of the vestibular device of FIG. 1. In the upper right of the figure (e.g., second sensor device) is a NELLCOR OxiMAX™ N-600 Pulse Oximeter, the middle shelf includes a cRIO FPGA (e.g., field programmable gate array computing device) and motor controller, and the bottom shelf includes an isolation transformer and power on/off switch.

Figure 3A:
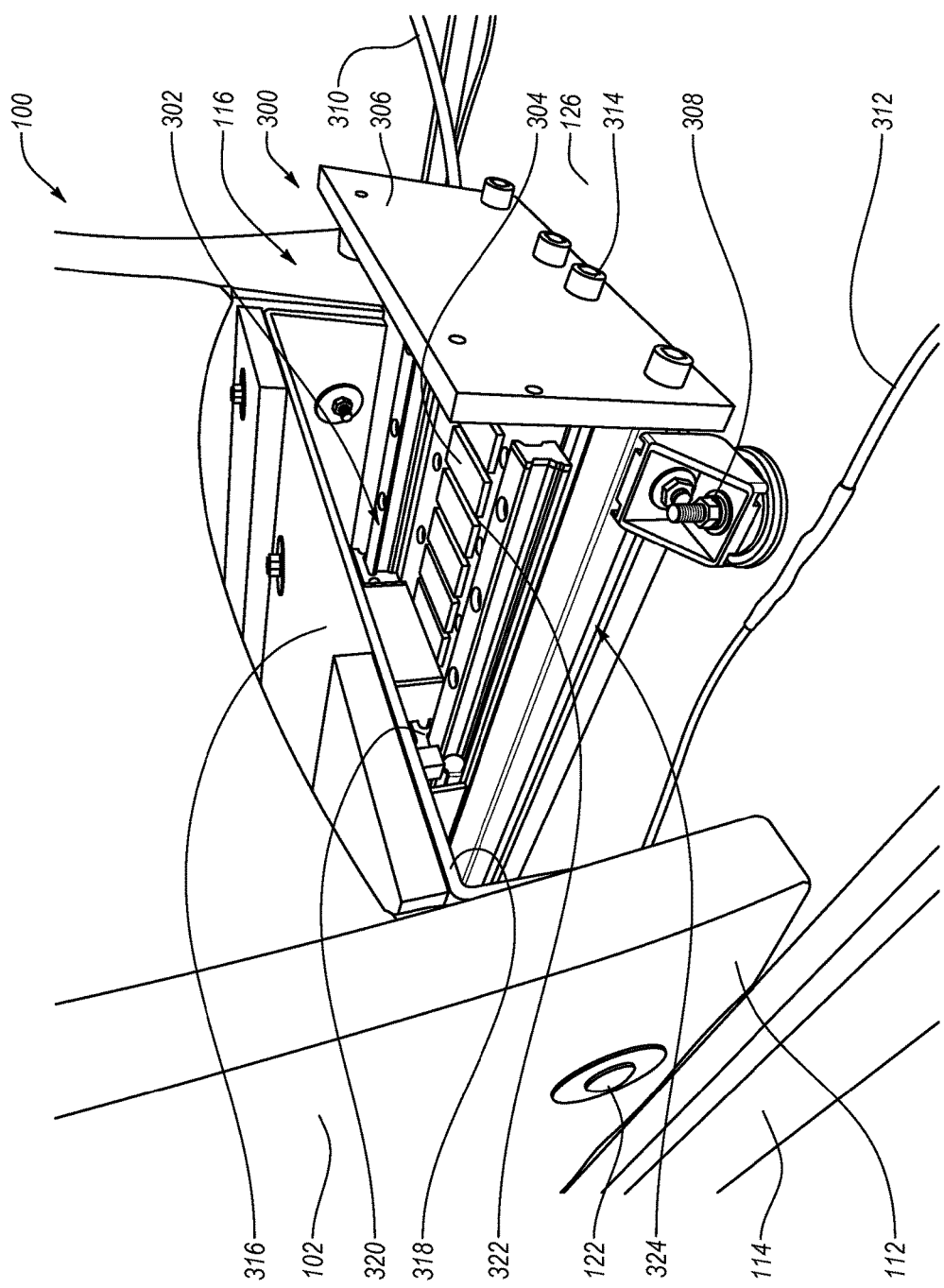
FIGS. 3A-3B show aspects of an embodiment of a stimulation device.
Figure 3B:
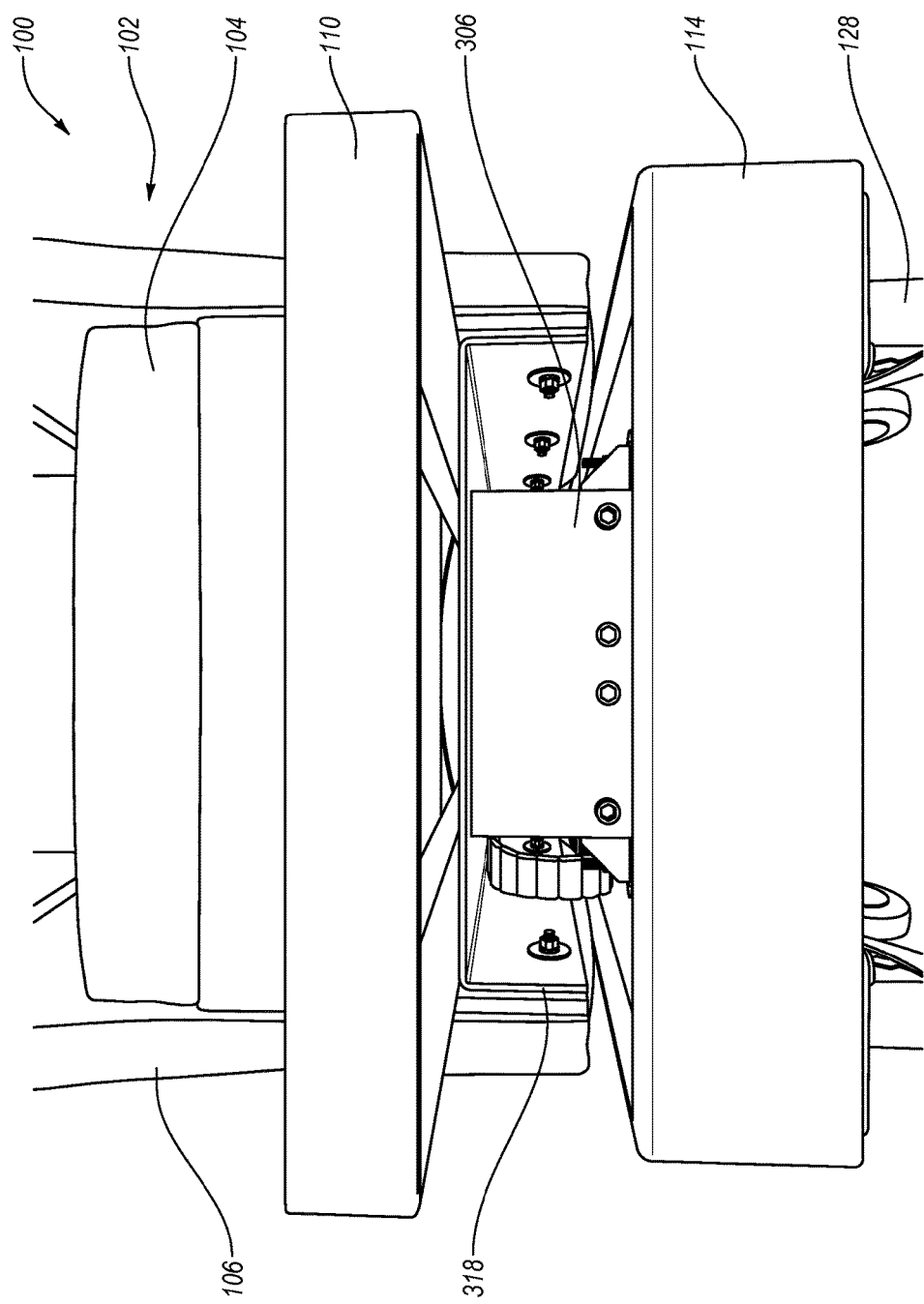

FIGS. 3A-3B show aspects of an embodiment of a vestibular stimulation device 100. The vestibular stimulation device 100 can include a motor system 300 that can move the chair 102 relative to the platform 114. The motor system 300 can include a motor 302, such as a linear motor. The motor system 300 can include a rail system 304 moveably coupled to the motor 302 so that the chair 102 can slide on the rail system 304 under operation by the motor 302 with respect to the platform 114. The rail system 304 can be functionally coupled to the chair with a rail mount 318 that has or is coupled to a rail member 320 that slides within a rail guide 322. The motor system 300 can include a governor 306 that restricts the movement or distance of movement that the chair 102 is capable of achieving with respect to the platform 114. The governor 306 can be coupled to the motor 302 and/or rail 304 via a governor coupler 314. A coupler 308 can be used to couple the motor system 300, such as the motor 302, to the platform 114. Such a coupler 308 can be received into a coupler groove 324 on the motor 302 so that adjustments in relative position of the chair 102 and platform 114 can be made. The motor 302 can receive instructional data for operation via a motor control wire 310. Other sensors can send and/or receive data via a data wire 312. The chair 102 can also include a foot rest receiver 316 that is configured to receive the foot rest 110.

Generally, FIGS. 3A-3B show a 3-phase DC linear motor and dual-rail linear translation stage. The DC linear motor can be exemplified by a H2W 3-Phase Brushless DC Linear Motor. The dual-rail linear translation stage is bolted to base of the chair and coupled to the linear motor.

Figure 4:
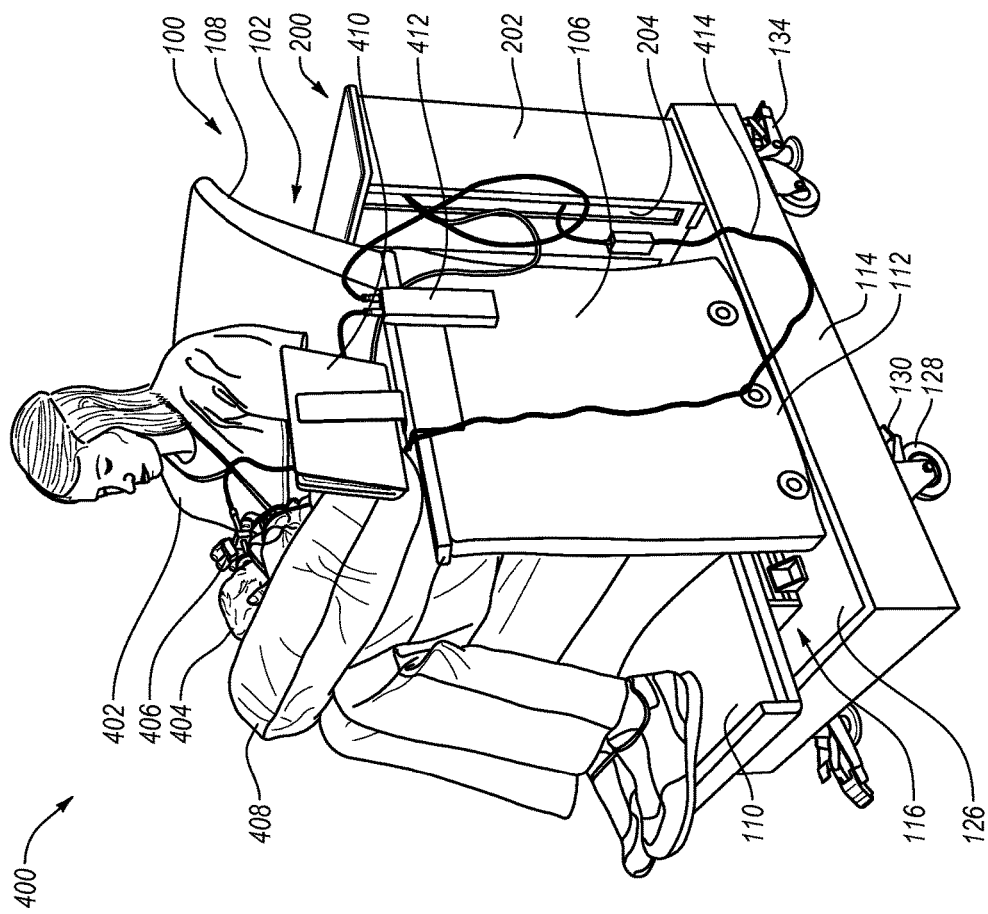
FIG. 4 shows an embodiment of an environment of using a stimulation system.

FIG. 4 shows an embodiment of an environment 400 of using a vestibular stimulation system. The environment 400 can include a medical professional 402 sitting in the chair 102 of the vestibular stimulation device 100. The medical professional 402 is holding an infant 404 that is sucking on an accelerometer pacifier 406 with the infant 404 on a pillow 408, such as a C-pillow (e.g., Boppy) in order to hold the infant 404 at an inclined position. The inclined position can range from about 20 degrees to about 40 degrees, from about 25 degrees to about 35 degrees, or about 30 degrees. A custom shaped pillow or other support can be used in place of the C-pillow so that the incline angle can be set. Also, the shaped pillow or support can be placed directly on the chair 102. The environment 300 can also include the chair 102 having a computing interface 410 mounted thereto, and which is operably coupled to the computing system 204 via controller data line 414. For example, the computing interface 410 can be a tablet computer or a laptop. Also shown is the sensor data line coupler 412 that can be coupled to any of the sensors that sense parameters of the infant 404, such as being coupled to the accelerometer pacifier 406 or other sensors.

Figure 5A:
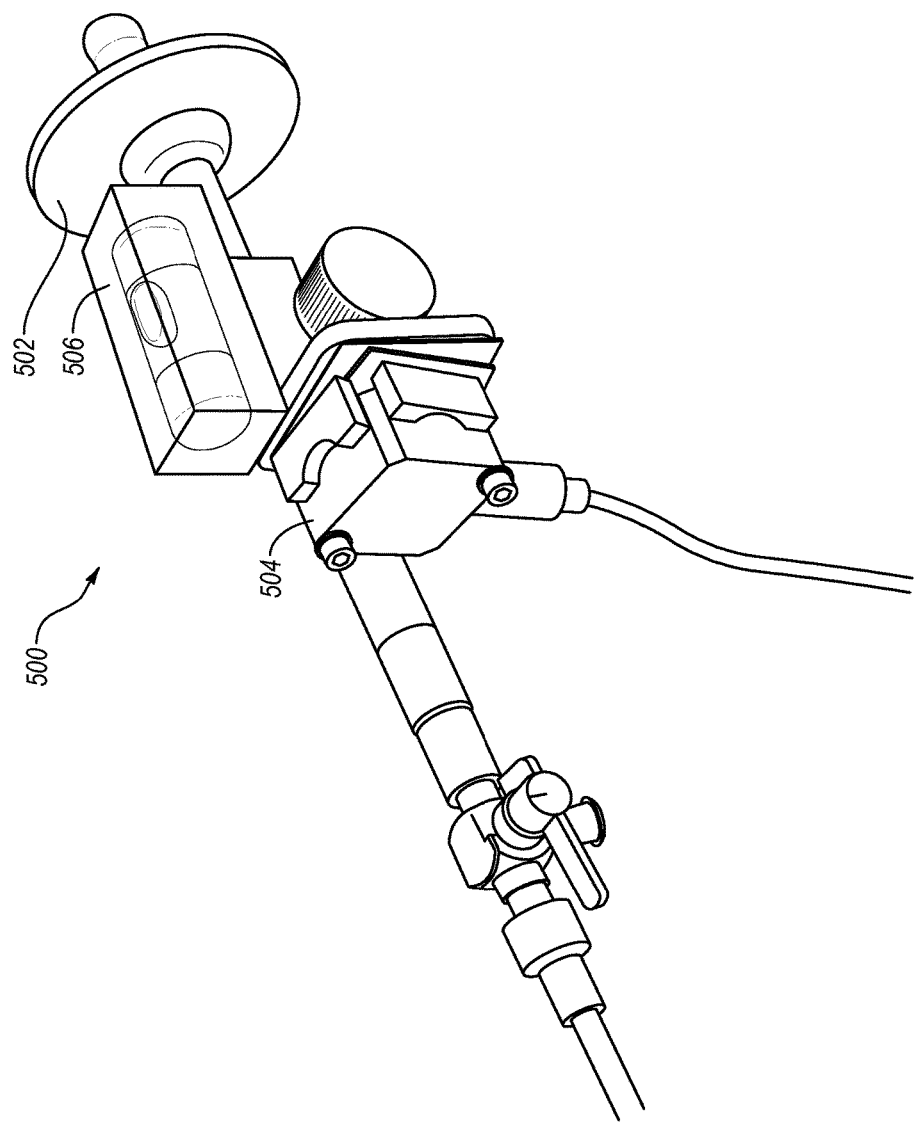
FIG. 5A shows an embodiment of a pacifier accelerometer.

FIG. 5A shows an embodiment of a pacifier accelerometer 500. The pacifier accelerometer 500 can include a pacifier 502 that is operably coupled to an accelerometer 504. The pacifier accelerometer 500 also includes a level 506, such as a bubble level, in order for the pacifier accelerometer 500 to be maintained to be substantially level during use. The level 506 can be a digital level that provides level data to the computing system.

FIG. 5B shows an embodiment of chest wall (e.g., rib cage+abdomen) respiration sensors 508, 512, where one is a rib cage respiration sensor 508 and the other is an abdomen respiration sensor 512. Each of the sensors 508, 512 includes a data line 510, 514 in order to be operably coupled with the computing system 204.

FIG. 6 shows an environment 600 with an infant 602 using a pacifier accelerometer 500 as described in FIG. 5A. The pacifier accelerometer 500 can include the pacifier 604, level, 606, and accelerometer 608. As shown, the accelerometer 608 can be coupled to a sensor line 612 via a sensor coupler 610. The sensor line 612 can be operably coupled with the computing system. Also shown is the infant 602 wearing the chest respiration band sensor 616 and the abdomen respiration band sensor 618, which are shown in dashed lines. While not essential, but useful, the baby is wrapped in a swaddle 614 or blanket to keep them in a developmentally supportive position and pacified.

Figure 7:
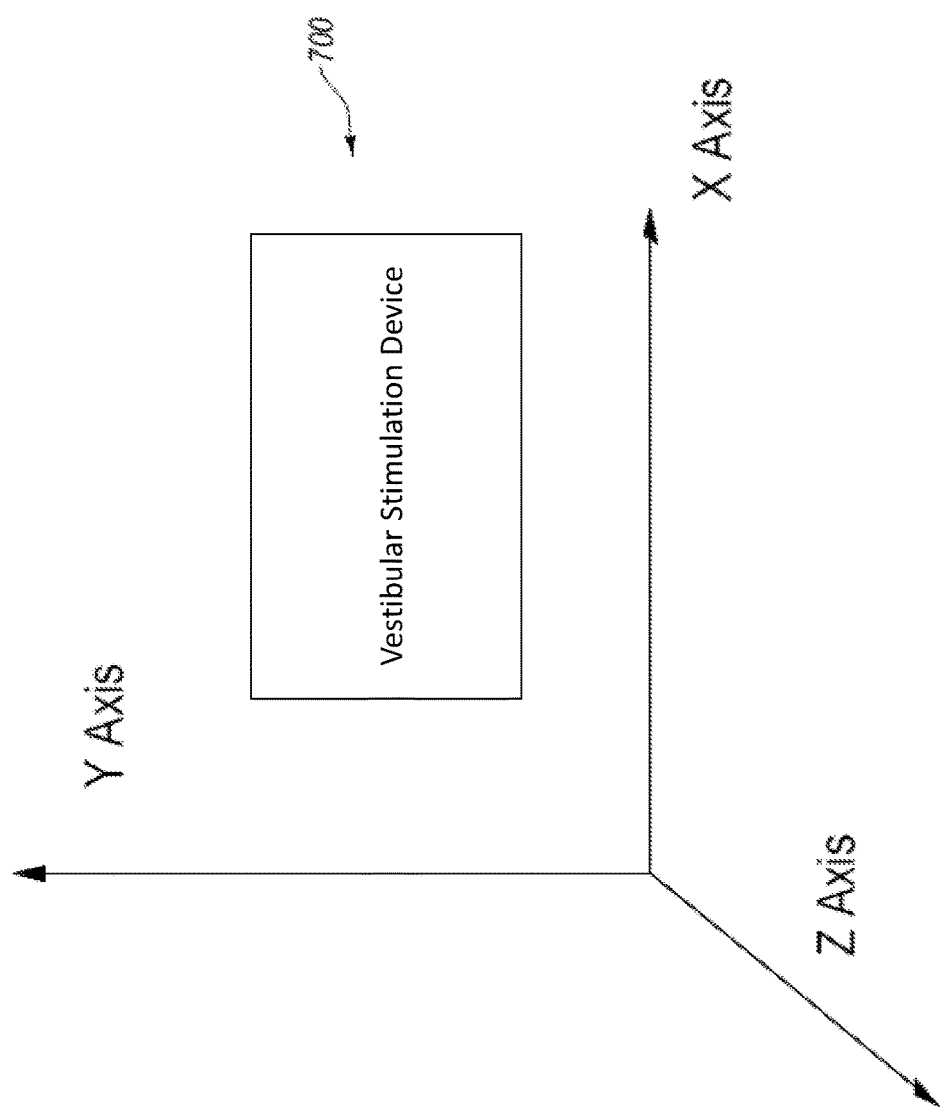
FIG. 7 shows a stimulation device and movement degrees of freedom.

FIG. 7 shows a vestibular stimulation device 700 and movement degrees of freedom. The vestibular stimulation device 700 can be a chair, crib, or isolette or the like which can be moved by a mechanical system in the X, Y, and Z axes.

Figure 8A:
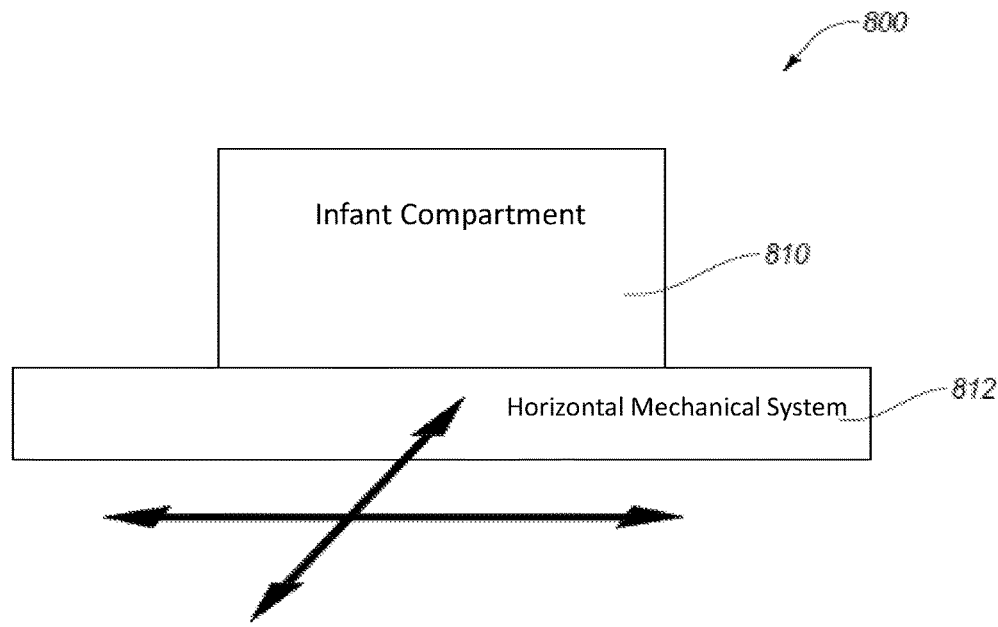
FIG. 8A shows an embodiment of a stimulation device with two degrees of freedom.

FIG. 8A shows an embodiment of a vestibular stimulation device 800 with two degrees of freedom. The vestibular stimulation devices 100 can include an infant compartment 810 operably mounted mechanical system 812 that is capable of moving in 2 dimensions, this can include linear movements or oscillatory, circular or other 2 dimensional movements.

Figure 8B:
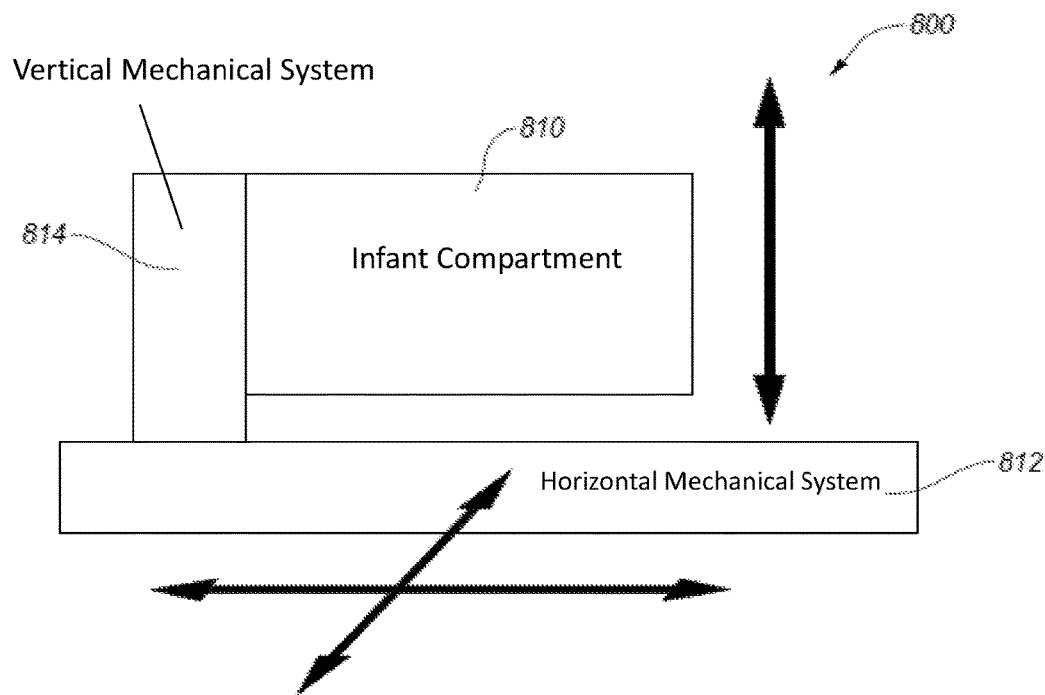
FIG. 8B shows an embodiment of a stimulation device with three degrees of freedom.

FIG. 8B shows an embodiment of a vestibular stimulation device 800 with three degrees of freedom. The vestibular stimulation device 800 can include an infant compartment 810 operably mounted a horizontal mechanical system 812 that is capable of moving in 2 dimensions and a vertical mechanical system 814 that is capable of moving vertically. The horizontal or mechanical system 812, 814, can include linear movements or oscillatory, circular or other dimensional movement. Also, a single mechanical system can include the features of the horizontal and mechanical systems 812, 814. The components of FIGS. 8A and 8B are shown as general blocks because any type of device of mechanical system can be used without limitation as long as the functionality described herein can be achieved.

It has been found that therapy with the vestibular stimulation device can be beneficial for improving the respiration of an infant, such as a premature infant. The vestibular stimulation device has demonstrated that linear acceleration stimuli can significantly affect respiratory patterning as evidenced by increased rate of abdominal movements during breathing, improved infant state control, and a shorter length of hospitalization.

The vestibular stimulation device can be configured to provide therapeutic stimulation of the vestibular system in infants, such as premature infants. In one embodiment, the vestibular device incorporates a servo-controlled linear stage mounted to the base of a medical-grade glider chair to produce highly controlled gliding motions in the horizontal plane. A PC-interfaced National Instruments cRIO FPGA (field programmable gate array) is programmed as a motion control and data acquisition system. The vestibular device can provide linear motion by being programmed to generate sinusoidal rates of about 30, 39, 48, or 57 cycles per minute (cpm), or any value therebetween. The sinusoidal rates can range from about 25 to about 60 cpm, about 30 to about 55 cpm, about 30 to about 50 cpm, or about 35 to about 45 cpm, or about 40 cpm, or any value therebetween. The vestibular stimulation device can be configured to provide a range of displacements, such as displacements corresponding to 88.90, 53.34, 34.04, and 24.64 mm, or any value therebetween or other values or integers. Vestibular stimulation device can provide displacements ranging from 20 mm to 90 mm, about 30 mm to about 80 mm, about 40 mm to about 70 mm, about 50 mm to about 60 mm, or about 55 mm, or any value therebetween.

The cycles and displacement can be paired as follows: 30 cpm with 88.9 mm displacement; 39 cpm with 53.34 mm displacement; 48 cpm with 34.04 mm displacement; and 57 cpm with 24.64 mm displacement. These stimulus parameters can provide a peak acceleration of about 0.36 meters per second squared ($m/s^2$) at each rate. The selected frequencies can be within the expected range for chest wall motion during infant's respiration (e.g., 40-60 breaths per minute (BPM)).

The vestibular stimulation device can provide these cycles and displacements to stabilize and accelerate chest wall (e.g., rib cage and abdomen) motor patterning during respiration. Also, the vestibular stimulation device can improve neonate behavioral state control (e.g., sleep-wake cycling). The vestibular stimulation device can reduce the infant's length of stay in the hospital after birth, such as after a preterm birth. As such, the vestibular stimulation device can overcome at least one form of sensory deprivation in the NICU by providing the newborn infant with needed vestibular stimulation to promote neurologic development (e.g., improved postural control, modulation of reticular formation via premotor inputs, etc.).

In one example, the vestibular stimulation device can include an integrated position-servo motor operably coupled with a digital controller to generate physiologically appropriate sinusoidal displacements of the glider chair in the horizontal plane at specified rates (e.g., 0.5, 0.65, 0.8, and 0.95 Hz) and accelerations (0.21, 0.36, and 0.51 $m/s^2$). The associated rates of movement in any direction can range from about 0.25 Hz to about 1 Hz, from about 0.5 Hz to about 0.95 Hz, from about 0.65 Hz to about 0.8 Hz, or around 0.7 Hz. The accelerations can range from 0.15 $m/s^2$ to about 0.70 $m/s^2$, from about 0.2 $m/s^2$ to about 0.6 $m/s^2$, from about 0.25 m/s² to about 0.5 m/s², from about 0.3 m/s² to about 0.4 m/s² or about 0.35 m/s², where 0.36 m/s² may be preferred.

In one example, twelve preterm infants (7F/5M, birth GA 32; 6, BW 1927 g) were recruited from the NICU at Stormont-Vail Regional Hospital in Topeka for a vestibular stimulation study. The study was designed to investigate the role of vestibular stimulation on sensorimotor integration of the respiratory central pattern generator (rCPG) through physiologically appropriate rates (e.g., 30, 39, 48, 57 cycles/min) and peak accelerations (e.g., 0.21, 0.36, 0.51 m/s²). Many research studies have shown the potent influences vestibular stimulation has on the rCPG; however, none have provided linear gliding sinusoidal stimulus with modifications to rate and acceleration while measuring breaths per minute (BPM) and oromotor control. The length of hospitalization was monitored to show that vestibular stimulation can reduce the length of hospitalization after pre-term birth.

Each infant received a 15 minute gliding protocol starting at 32 weeks PMA, three times a day (i.e., 3x/day) before a scheduled feed for at least 10 days over two weeks. Infants were fitted with two soft cloth Respitrace™ inductance bands around the rib cage and abdomen to measure respiratory rate. The gliding protocol alternates between baseline and stimulus conditions every minute. During baseline conditions, the glider chair was stationary. Respiration, suck dynamics, and pulse-oximetry were recorded and monitored throughout the study.

The 15 minute gliding protocol alternated between baseline (B1-B8) and stimulus (S1-S7) conditions every minute. During the baseline conditions, the glider chair did not move and only respiration and suck were monitored. Overall, there were seven gliding stimuli and eight baseline conditions. Stimulation order among the baseline conditions was varied among participants and session by using 15 different stimulus sequences that were presented to the infants in a counterbalanced sequence.

Chest wall displacements transduced by the clinical Respitrace™ device were digitized and BPM were analyzed for entire gliding protocol. The BPM were calculated by counting the number of inhalations that occurred in one minute using a peak detection software program in LabVIEW v.9.0.

Pulse and oxygen saturation (SpO2) signals were digitized and analyzed for the entire gliding protocol. Minute averages were attained for SpO2 and pulse for every baseline (B1-B8) and stimulus (S1-S7) condition.

Power spectrums are plots of the portion of a signal's power (energy per unit time) falling within given frequency bins. Power spectrums were calculated for the best 15 minutes of abdominal Respitrace™ data for the first baseline (B1), stimulus (S1-S7), and the post-baseline conditions (B2-B8). All abdominal waveforms were plotted. Records with movement artifact, or episodes of apnea were discarded leaving the most patterned 15 minutes of respiratory output for extended data analysis. The data were then pooled across infants to examine the amplitude of the spectra. The abdominal Respitrace™ output was used for analysis because preterm infants are predominantly belly breathers. Abdominal respiratory waveforms were filtered with a digital Butterworth band-pass filter (0.6-4 Hz). Power spectrum plots were completed using MATLAB with a frequency resolution of 0.03 Hz.

On average, infants received 24 vestibular device sessions. It was found that stimulus condition had a significant effect for the in rib cage [$F (7, 77)=25.53$, $p<0.01$] and abdominal [$F (7, 77)=23.60$, $p<0.01$] breaths per minute (BPM). In general, infants increased their respiratory rate in response to the vestibular device stimulus. Table 1 shows the linear (horizontal) gliding stimulus parameters. Stimulus 7 (0.51 m/s2 @ 0.65 Hz) provided the highest acceleration to the infant and induced significantly higher BPM than Stimulus 1 (0.36 m/s² @ 0.50 Hz), 4 (0.36 m/s² @ 0.95 Hz), and 5 (0.21 m/s² @ 0.65 Hz) for the rib cage, and Stimuli 1 and Stimulus 4 for the abdomen. It is clear from the data that acceleration rather than cycle frequency has the largest influence over the rCPG and is capable of inducing significant changes in chest wall kinematics. In spite of the increases in BPM during vestibular stimulation, infants maintained stable oxygen saturation (SpO2) and pulse rate throughout the vestibular stimulation study. It has now been determined that infants are able to modify their respiratory rate in response to vestibular stimulus while maintaining their SpO2 and pulse. All infants were offered a pacifier accelerometer during each vestibular device session. Vestibular stimulation had no significant effect on non-nutritive suck development as measured by acceleration of suck on the pacifier.

The length of stay in the NICU was measured from the admission date (e.g., birth date) to the discharge date for all infants in the vestibular stimulation study and the untreated preterm control infants. Infants that used the vestibular stimulation device were discharged from the hospital nine days sooner than the control infants resulting in a substantial reduction in hospitalization costs (~$40,000/infant). Overall, vestibular stimulation delivered to the preterm infant between 32 and 34 weeks PMA effectively modulates respiratory rate, resets the rCPG, and shortens hospitalization.

The major components of the vestibular stimulation device include a medical glider chair, linear servo motor (H2W Technologies, Inc., Santa Clarita, Calif.), servo electronics, a PC-interfaced National Instruments cRIO FPGA (field programmable gate array) programmed as a motion control and data acquisition system, and a software GUI and program interface programmed in LabVIEW v.9.0. The PC-based data acquisition computer allowed for quick touchpad operation and real-time data display of the infant's physiology. A screen shot of the graphical user interface of the computing device (e.g., tablet PC) during a vestibular device stimulation session is shown in FIG. 2B.

The computing system can include a servo controller that can be programmed to generate the control signal protocol to 'glide' the chair according to sinusoidal input functions at rates from 0.5 to 0.95 cycles per second at glide displacements ranging from 2.4 cm to 8.9 cm. A power spectrum can be performed on the glider signals to ensure that the power spectrum frequencies match the desired stimulus rates. The provisional application, which is incorporated herein by specific reference shows a glider waveform linear encoder signals for actual chair displacement and power spectrum for the entire gliding stimulus. The frequency resolution is 0.05 Hz.

For safety, the servo motor of the mechanical system can include an electronic safety limiter (e.g., governor) to limit the rate at 1.5 Hz, and the linear motor can include mechanical stops to limit displacement of the glider translation stage to 14 cm. The resulting stimulus regimen delivered by the glider chair includes linear accelerations and cyclic rates well below the vestibular stimulation possible with a conventional rocking chair in the clinic or home. The data acquisition microprocessor (National Instruments cRIO) can be programmed to synthesize control signals for the linear motor and perform all real-time digitization of the biological signals, including NNS compression pressure, Respitrace™

Chest wall displacement for rib cage and abdomen, and pulse-oxygen signals at 50 Hz/channel at 16-bits of voltage resolution. A medial grade isolation transformer can be configured between the AC-line source and all signal conditioning and digital electronics.

It has been found that infant positioning in the incline angle can be important. During the study described, preterm infants were placed on the researcher's lap, by either the nursing staff or the infant's parents/caregiver, in a semi-inclined position against a C-shaped pillow (e.g., Boppy) as shown. The pillow was fitted with a hypoallergenic water-resistant cover as well as a cotton cloth cover, both of which were gas sterilized with ethylene oxide prior to the enrollment of a new infant. The pillow was configured to provide ergonomic semi-inclined positioning for the infant but also considered the standard in infant feeding pillows used in the NICU and various feeding clinics. However, any type of support, such as a custom support can be used to provide an incline angle to the infant. The custom support may also be configured to have ergonomic contours so that the support can be placed directly on the chair or other holder member.

An accelerometer was adapted for use with a pacifier so that signals from the infant could be matched with signals from the glider. In an effort to assess the acceleration the infant received during the gliding stimulus, an accelerometer was mounted to the infant's pacifier receiver as shown in FIG. 6. A level was mounted on the pacifier to monitor accelerometer-pacifier receiver position relative to the horizontal plane. The location of the accelerometer provided a good estimate of head acceleration without having to position the accelerometer directly on the infant's head. The uniaxial PBS piezotronics (Model 3711B122G) accelerometer was mounted to a specially machined member attached to the pacifier receiver using Velcro contact pad. A line bubble meter (e.g., a construction bubble level) was mounted to the receiver to ensure the accelerometer was held on the appropriate plane. The infant's pacifier was attached to the machined member and offered to the infant every session.

Infant preparation and positioning can be important for the vestibular device stimulation therapy. During the gliding protocol, the infant was swaddled in a blanket, with limbs positioned at midline, background/overhead lighting dimmed to promote eye contact with the tester and placed in a supportive semi-inclined position against the C-shaped pillow. The gliding stimulus was not initiated until the infant was in an optimal behavior sate, i.e., drowsey to active alert (e.g., state 3, 4, or 5 as described by the Naturalistic Observation of Newborn Behavior, Newborn Individualized Development Care and Assessment Program (NIDCAP).

It was found that infants that receive the vestibular device stimulation therapy were able to leave the NICU sooner than infants not receiving the vestibular stimulation therapy. The length of stay in the NICU was measured from admission date (birth date) to discharge date for all infants in this study, and were compared to the cohort of untreated preterm infants matched for birth.

In one embodiment, a vestibular stimulation device can include: an holder member or other compartment configured to contain an infant; one or more medical sensors configured to be associated with the infant in the compartment; a mechanical system attached to the compartment such that the mechanical system is capable of moving the compartment in one or more directions; and a computing system configured to control the mechanical system and to obtain data from the one or more sensors. The compartment can be configured as a crib, cradle, isolette (NICU isolation chamber for infants), bed, chair, table top with one or more restraints, or combination thereof. The device can include a timer that is configured to start motion in one or more directions at a first time and to stop motion at a second time.

The mechanical system can be configured to provide movement so as to provide imposed motion, acceleration, and/or change in orientation to a gravitational field. Also, the mechanical system can be configured to move the compartment in the X-axis, Y-axis, and/or Z-axis. The mechanical system can be configured to move the compartment in a linear motion, or nonlinear motion may be used. The mechanical system can be configured to move the compartment in each axis independently, or move the compartment in two or more directions simultaneously. The mechanical system can be configured to move the compartment in a sinusoidal displacement. The mechanical system is configured to move the compartment in a sinusoidal displacement at a rate of from about 0.5 to about 0.95 Hz. The mechanical system can be configured to move the compartment with accelerations from about 0.21 to about 0.51 m/s$^2$. The mechanical system can be configured to move the compartment with sinusoidal cycles from about 30 to about 60 cycles per minute (cpm). The mechanical system can be configured to move the compartment with a displacement from 20 mm to about 90 mm. The mechanical system can be configured to move the compartment with a servo motor. The mechanical system can be configured to move the compartment to simulate motion, acceleration, and changing orientation to gravitational loads. The mechanical system can be configured to move the compartment to simulate vestibular stimulation through routine motor activities, such as walking, driving a car, sitting, sleeping, rolling over, postural changes, breathing, or the like.

The mechanical system can include one or more integrated position-servo motors and digital controllers. The mechanical system can include a linear movement driver. The mechanical system can include at least one servo motor for each direction of movement. The mechanical system can be configured to be inaudible so as to not affect a therapeutic treatment, which can be beneficial to not disturb or irritate the infant. The mechanical system can include a glider track for the container.

A computing system can be operably coupled to the mechanical system so as to control the mechanical system. The computing system can be operably coupled to the mechanical system so as to be capable of receiving data therefrom. The computing system can include a data acquisition microprocessor programmed to synthesize control signals for the linear motor and perform all real-time digitization of the biological signals.

The computing system and mechanical system can be configured to provide motion to the compartment at frequencies within a range of chest wall motion for an infant. For example, the compartment can move at a frequency equivalent to about 40 to 60 breaths per minute (BPM). The computing system and mechanical system can be configured to receive data during a vestibular stimulation treatment, where the data can include the number of breaths per minute (BPM), oromotor control, suck displacement, and/or length of time in therapy, NICU stay, and/or hospital stay. The computing system and/or mechanical system can be configured to limit the rate, displacement, or other parameter of compartment motion.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 9:
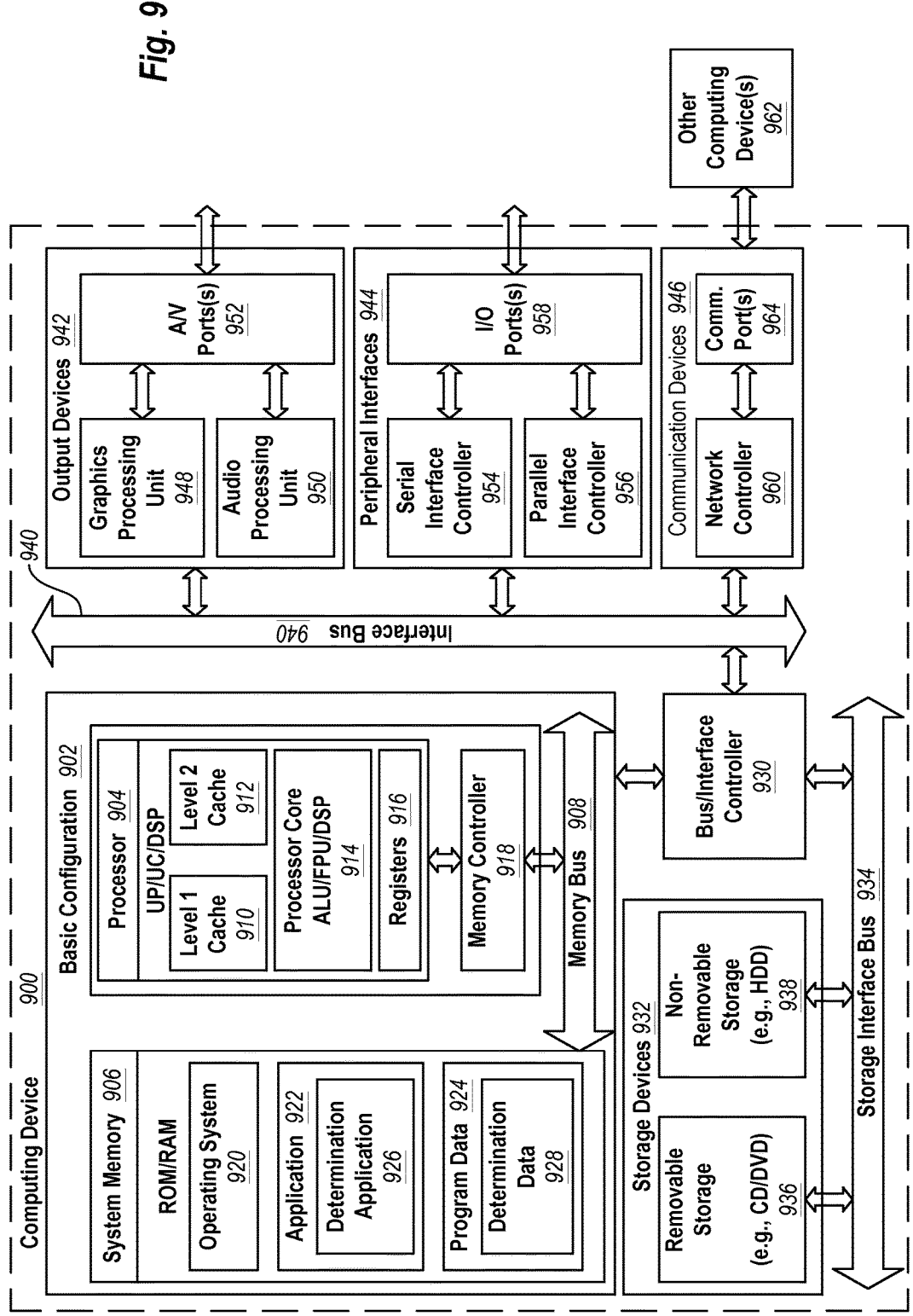
FIG. 9 shows an embodiment of a computing device that can operate with a stimulation system.

FIG. 9 shows an example computing device 900 that is arranged to perform any of the computing methods described herein. The computing system 900 can represent a user side computing device, such as a mobile computer. In a very basic configuration 902, computing device 900 generally includes one or more processors 904 and a system memory 906. A memory bus 908 may be used for communicating between processor 904 and system memory 906.

Depending on the desired configuration, processor 904 may be of any type including but not limited to a microprocessor (µP), a microcontroller (µC), a digital signal processor (DSP), or any combination thereof. Processor 904 may include one more levels of caching, such as a level one cache 910 and a level two cache 912, a processor core 914, and registers 916. An example processor core 914 may include an arithmetic logic unit (ALU), a floating point unit (FPU), a digital signal processing core (DSP Core), or any combination thereof. An example memory controller 918 may also be used with processor 904, or in some implementations memory controller 918 may be an internal part of processor 904.

Depending on the desired configuration, system memory 906 may be of any type including but not limited to volatile memory (such as RAM), non-volatile memory (such as ROM, flash memory, etc.) or any combination thereof. System memory 906 may include an operating system 920, one or more applications 922, and program data 924. Application 922 may include a determination application 926 that is arranged to perform the functions as described herein including those described with respect to methods described herein. Program Data 924 may include determination information 928 that may be useful for analyzing the contamination characteristics provided by the sensor unit 940. In some embodiments, application 922 may be arranged to operate with program data 924 on an operating system 920 such that the work performed by untrusted computing nodes can be verified as described herein. This described basic configuration 902 is illustrated in FIG. 9 by those components within the inner dashed line.

Computing device 900 may have additional features or functionality, and additional interfaces to facilitate communications between basic configuration 902 and any required devices and interfaces. For example, a bus/interface controller 930 may be used to facilitate communications between basic configuration 902 and one or more data storage devices 932 via a storage interface bus 934. Data storage devices 932 may be removable storage devices 936, non-removable storage devices 938, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 906, removable storage devices 936 and non-removable storage devices 938 are examples of computer storage media. Computer storage media includes, but is not limited to, RAM, ROM, EEPROM, flash memory, solid state drives (SSDs) or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of computing device 900.

Computing device 900 may also include an interface bus 940 for facilitating communication from various interface devices (e.g., output devices 942, peripheral interfaces 944, and communication devices 946) to basic configuration 902 via bus/interface controller 930. Example output devices 942 include a graphics processing unit 948 and an audio processing unit 950, which may be configured to communicate to various external devices such as a display or speakers via one or more A/V ports 952. Example peripheral interfaces 944 include a serial interface controller 954 or a parallel interface controller 956, which may be configured to communicate with external devices such as input devices (e.g., keyboard, mouse, pen, voice input device, touch input device, etc.) or other peripheral devices (e.g., printer, scanner, etc.) via one or more I/O ports 958. An example communication device 946 includes a network controller 960, which may be arranged to facilitate communications with one or more other computing devices 962 over a network communication link via one or more communication ports 964.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 900 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 900 may also be implemented as a personal computer including both laptop computer and non-laptop computer configurations.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an"

limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims Korner, A. F., Schneider, P., a Forrest, T. (1983). Effects of vestibular-proprioceptive stimulation on the neurobehavioral development of preterm infants: a pilot study. Neuropediatrics, 14(3), 170-175.

TABLE 1

Linear (horizontal plane) gliding stimuli.

| Glider Stimulus (S) | Frequency (Hz) | Cycles/Min | Displacement (mm) | Peak Acceleration (m/s$^2$) |
|---|---|---|---|---|
| 1 | 0.50 | 30 | 88.90 | 0.36 |
| 2 | 0.65 | 39 | 53.34 | 0.36 |
| 3 | 0.80 | 48 | 34.04 | 0.36 |
| 4 | 0.95 | 57 | 24.64 | 0.36 |
| 5 | 0.65 | 39 | 27.94 | 0.21 |
| 6 | 0.65 | 39 | 53.34 | 0.36 |
| 7 | 0.65 | 39 | 75.44 | 0.51 |

The invention claimed is:

1. A vestibular stimulation device comprising:
a holder member adapted to hold a living subject;
a platform;
a mechanical system operably coupling the holder member to the platform such that the mechanical system is capable of moving the holder member in one or more directions relative to the platform;
one or more sensors adapted to be associated with the living subject and detect one or more parameters of the living subject; and
a computing system having a user input and/or output interface operably coupled to the mechanical system and the one or more sensors so as to provide mechanical data to the mechanical system in order to control movement of the holder member relative to the platform and to collect the one or more parameters of the living subject from the one or more sensors, wherein the mechanical system includes a linear motor and a glider track configured to move the holder member linearly with respect to the platform in one or more sinusoidal movement patterns under control of the computing system.

2. The vestibular stimulation device of claim 1, wherein the holder member is configured as at least one of a crib, cradle, isolette, bed, chair, or table top with one or more restraints, and the living subject is an infant.

3. The vestibular stimulation device of claim 2, wherein the mechanical system is configured to move the holder member in the directions of an X-axis, Y-axis, and/or Z-axis.

4. The vestibular stimulation device of claim 3, wherein the mechanical system is configured for one or more of the following:
to move the holder member in a sinusoidal displacement at a rate of from about 0.5 to about 0.95 Hz;
to move the holder member with accelerations from about 0.21 to about 0.51 m/s$^2$;
to move the holder member with sinusoidal cycles from about 30 to about 60 cycles per minute (cpm);
to move the holder member with a displacement from 20 mm to about 90 mm;
to move the holder member so as to simulate motion, acceleration, and changing orientation to gravitational loads;
to move the holder member at frequencies with a range of chest wall motion for an infant human living subject; or
to move the holder member at frequencies equivalent to about 40 to 60 breaths per minute (BPM).

5. The vestibular stimulation device of claim 2, wherein the one or more sensors are selected from a sensor configured to detect acceleration, a sensor configured to detect breaths per minute (BPM), a sensor configured to detect suck displacement, a sensor configured to detect oromotor control, a sensor to measure pulse, oxygenation of hemoglobin, blood oxygen saturation, living subject head tilt, or combinations thereof, and wherein the computing system is configured to receive, store, and process data of the one or more sensors independently or in combination.

6. A vestibular stimulation system comprising the vestibular stimulation device of claim 2, further comprising:
a pacifier having an accelerometer sensor configured to detect acceleration.

7. The vestibular stimulation system of claim 6, comprising:
a computer-readable medium having a computer program product comprising computer executable instructions for performing a computing method for operating the vestibular stimulation system, the computer executable instructions comprising instruction data for the mechanical system to perform one or more of the following:
to move the holder member in a sinusoidal displacement at a rate of from about 0.5 to about 0.95 Hz;
to move the holder member with accelerations from about 0.21 to about 0.51 m/s$^2$;
to move the compartment with sinusoidal cycles from about 30 to about 60 cycles per minute (cpm);
to move the compartment with a displacement from 20 mm to about 90 mm;
to simulate motion, acceleration, and changing orientation to gravitational loads;
to move at frequencies with a range of chest wall motion for an infant human living subject; or
to move at frequencies equivalent to about 40 to 60 breaths per minute (BPM).

8. The vestibular stimulation system of claim 7, comprising:
computer executable instructions comprising instructions for the computing system to receive, store, and process data of the one or more sensors independently or in combination, wherein the one or more sensors are selected from a sensor configured to detect breaths per minute (BPM), a sensor configured to detect suck displacement, a sensor configured to detect oromotor control, a sensor to measure pulse, oxygenation of hemoglobin, blood oxygen saturation, living subject head tilt, or combinations thereof.

9. The vestibular stimulation system of claim 8, comprising a pillow configured to incline the infant when located on the holder member.

10. A pacifier accelerometer comprising:
a pacifier having a nipple;
an accelerometer operably coupled to the pacifier opposite of the nipple, the accelerometer having a longitudinal axis configured to be in a horizontal plane; and
a level operably coupled to the pacifier and/or accelerometer in a position so as to be parallel to the longitudinal axis such that the level is horizontal when the longitudinal axis of the accelerometer is horizontal.

11. The pacifier of one of claim 10, wherein the accelerometer is mounted opposite of the pacifier with the level mounted on the accelerometer.

12. A method for providing vestibular stimulation to a living subject, the method comprising:
providing the vestibular stimulation device of claim 1;
placing a living subject on the holder member;
associating one or more sensors to the living subject;
moving the holder member in the one or more directions so as to provide vestibular stimulation treatment to the living subject; and
obtaining sensor data from the one or more sensors.

13. The method of claim 12, wherein the vestibular stimulation is provided to an infant as the living subject in an amount and number of times sufficient for:
treating a respiratory complication in an infant;
improving formation of indirect neural pathways in the infant;
improving postural motor control in the infant;
improving state control in the infant;
improving respiratory patterns in the infant; or
improving oromotor development in the infant.

14. The method of claim 13, comprising selecting the infant to have one or more of the following characterizations:
the infant is dependent on significant amounts of oxygen;
the infant has a respiratory complication;
the infant is in need of improved formation of indirect neural pathways;
the infant is in need of improved postural motor control;
the infant is in need of improved state control;
the infant is in need of improved respiratory patterns; or
the infant is in need of improved oromotor development.

15. The method of claim 14, comprising one or more of the following:
moving the holder member in the X-axis, Y-axis, and/or Z-axis;
moving the holder member in a sinusoidal displacement at a rate of from about 0.5 to about 0.95 Hz;
moving the holder member with accelerations from about 0.21 to about 0.51 m/s$^2$;
moving the holder member with sinusoidal cycles from about 30 to about 60 cycles per minute (cpm);
moving the holder member with a displacement from 20 mm to about 90 mm;
moving the holder member so as to simulate motion, acceleration, and changing orientation to gravitational loads;
moving the holder member at frequencies with a range of chest wall motion for an infant human living subject; or
moving the holder member at frequencies equivalent to about 40 to 60 breaths per minute (BPM).

16. The method of claim 15, comprising collecting, storing, and/or analyzing sensor data, wherein the one or more sensors are selected from a sensor configured to detect acceleration, a sensor configured to detect breaths per minute (BPM), a sensor configured to detect suck displacement, a sensor configured to detect oromotor control, a sensor to measure pulse, oxygenation of hemoglobin, blood oxygen saturation, living subject head tilt, or combinations thereof.

17. The method of claim 16, comprising providing the vestibular stimulation treatment before a feeding the infant.

18. The method of claim 16, comprising one or more of the following:
fitting the infant with a respiratory trace device including two soft cloth inductance bands around the rib cage and abdomen and measuring breaths per minute (BPM);
fitting infant with pulse rate and SpO2 signal measuring devices and measuring pulse rate and SpO2;
fitting infant with a neonate oxygen sensor and measuring oxygen saturation; or
determining a baseline without vestibular stimulation.

19. The vestibular stimulation device of claim 1, further comprising one or more wheels operably coupled to the platform.

20. The vestibular stimulation device of claim 1, further comprising one or more lift-locks coupled to the platform such that the platform has a mobile configuration when the lift-locks are disengaged and a stationary configuration when the lift-locks are engaged so as to elevate the wheels and entire device above ground.

* * * * *